US00PP35334P2

(12) United States Plant Patent
Van Huylenbroeck

(10) Patent No.: US PP35,334 P2
(45) Date of Patent: Aug. 22, 2023

(54) ***HYDRANGEA* PLANT NAMED 'ILVOHPPRM'**

(50) Latin Name: ***Hydrangea* x *paniculata***
Varietal Denomination: ILVOHPPRM

(71) Applicant: Spring Meadow Nursery Inc., Grand Haven, MI (US)

(72) Inventor: Johan Van Huylenbroeck, Melle (BE)

( * ) Notice: Subject to any disclaimer, the term of this patent is extended or adjusted under 35 U.S.C. 154(b) by 0 days.

(21) Appl. No.: 18/087,447

(22) Filed: Dec. 22, 2022

(51) Int. Cl.
*A01H 5/02* (2018.01)
*A01H 6/48* (2018.01)

(52) U.S. Cl.
USPC ..... Plt./250
CPC ..... *A01H 6/48* (2018.05)

(58) Field of Classification Search
USPC ..... Plt./250
CPC ..... A01H 5/02
See application file for complete search history.

*Primary Examiner* — Kent L Bell
(74) *Attorney, Agent, or Firm* — Cassandra Bright

(57) ABSTRACT

A new and distinct cultivar of *Hydrangea* plant named 'ILVOHPPRM' is disclosed, characterized by large conical-shaped panicles with flowers that age from greenish-white, to white, to pinkish-red. Plants have upright habits, red immature stems, and dark green foliage with yellow-green venation. The new variety is a *Hydrangea*, typically produced as an outdoor ornamental plant.

5 Drawing Sheets

Latin name of the genus and species: *Hydrangea* x *paniculata*.

Variety denomination: 'ILVOHPPRM'.

BACKGROUND OF THE INVENTION

The new cultivar is a product of a planned breeding program conducted by the inventor in Melle, Belgium. The objective of the breeding program was to produce new *Hydrangea* varieties with good habits, and large panicles that age to vivid dark pink to red. The open-pollination resulting in the new variety was made during 2003.

The seed parent is the variety *Hydrangea paniculata* 'DVPPinky', U.S. Plant Pat. No. 16,166. The pollen parent cannot be identified as this new selection resulted from an open-pollination.

The new variety was found and selected by the inventor in 2005 at the same nursery in Melle, Belgium. Asexual reproduction of the new cultivar 'ILVOHPPRM' was first performed during 2008 in Melle, Belgium, by softwood cuttings. Through subsequent asexual propagation, multiple additional generations have been reproduced, having shown that the unique features of this cultivar are stable and reproduced true to type.

The first offer for sale occurred Jun. 21, 2022, in Grand Haven, Mich. This sale was made directly by the inventor or one who obtained the claimed invention directly or indirectly from the inventor. This sale and all public disclosures (made directly by the inventor or one who obtained the claimed invention directly or indirectly from the inventor) made between Jun. 21, 2022 and the filing of this application fall within the exception allowed under 35 U.S.C. 102(b)(1).

SUMMARY OF THE INVENTION

The cultivar 'ILVOHPPRM' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'ILVOHPPRM.' These characteristics in combination distinguish 'ILVOHPPRM' as a new and distinct *Hydrangea* cultivar:

1. Large, conical-shaped panicles.
2. Flowers age from greenish-white, to white, to pinkish-red.
3. Red stem color on new growth.

PARENT COMPARISON

Plants of the new cultivar *Hydrangea* 'ILVOHPPRM' are similar to the seed parent in most horticultural characteristics, however, plants of 'ILVOHPPRM' differ in the following:

1. Flower panicles of the new variety are larger than flower panicles of the seed parent.
2. Flower panicles of the new variety are denser than panicles of the seed parent.

COMMERCIAL COMPARISON

Plants of the new cultivar *Hydrangea* 'ILVOHPPRM' can be compared to the commercial variety *Hydrangea* 'RENSUN', U.S. Plant Pat. No. 25,438. Plants of 'ILVOHPPRM' are similar to plants of 'RENSUN' in most horticultural characteristics, however, plants of 'ILVOHPPRM' differ in the following:

1. Flower panicles of the new variety are larger than flower panicles of this comparator.
2. Sterile flower size of the new variety is larger than sterile flower size of this comparator.

BRIEF DESCRIPTION OF THE PHOTOGRAPHS

The accompanying photographs in FIGS. 1 and 2 illustrate typical plants of 'ILVOHPPRM' grown outdoors in Grand Haven, Mich. Plants are approximately 2-3 years old, grown in the ground in a trial field. FIGS. 3, 4 and 5 illustrate inflorescences of the new variety at different stages of maturity. The photographs were taken using conventional techniques and although colors may appear different from actual colors due to light reflectance it is as accurate as possible by conventional photographic techniques.

DETAILED BOTANICAL DESCRIPTION

Figure 1:
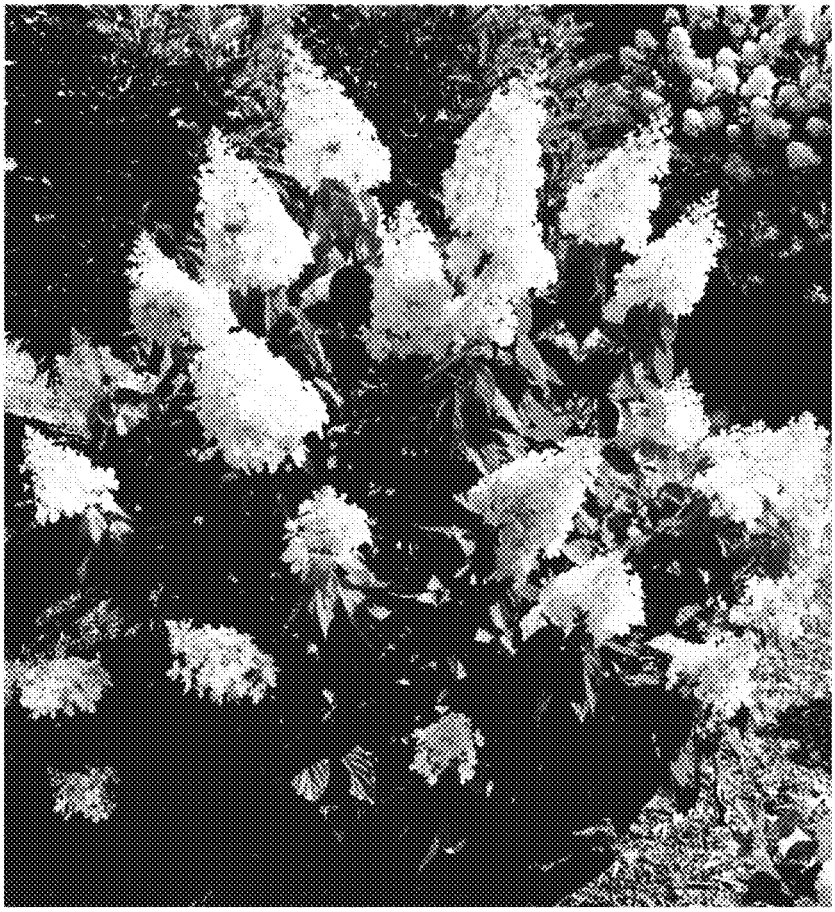
FIG. 1 illustrates a plant of 'ILVOHPPRM' with inflorescences in the earliest stage of maturity.
Figure 2:
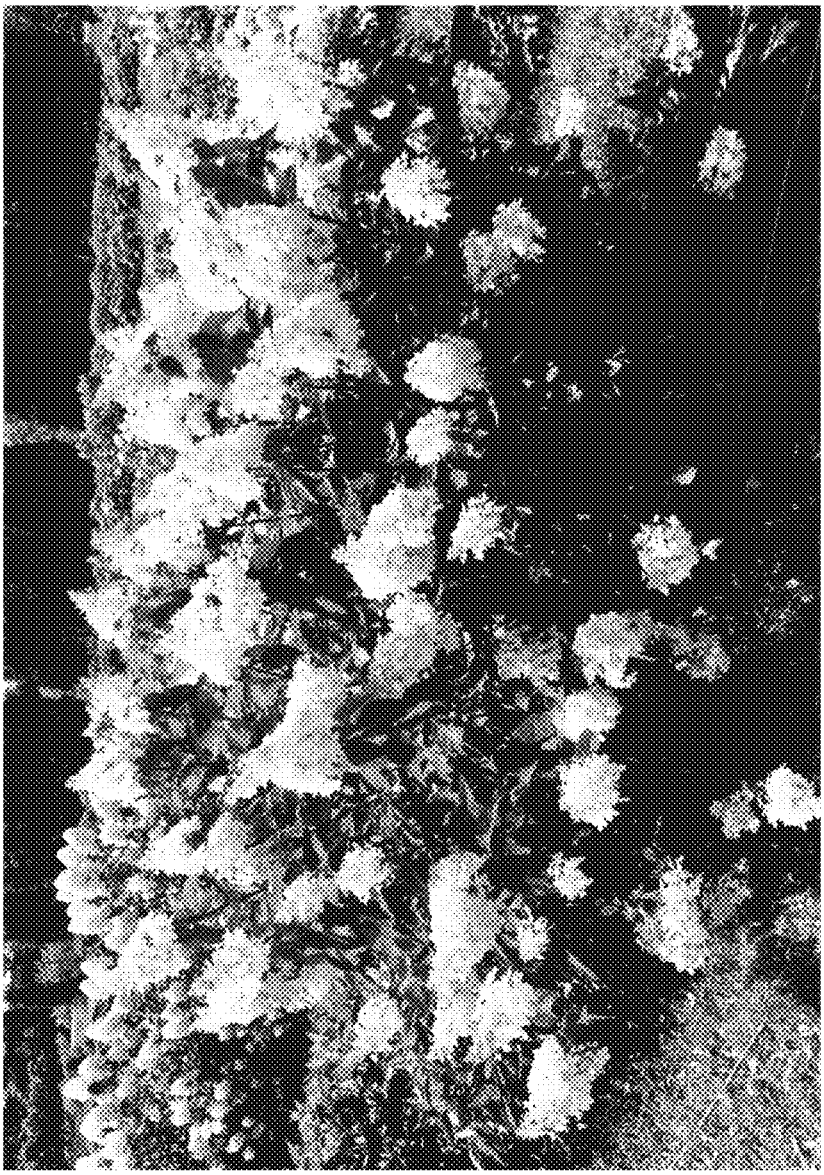
FIG. 2 illustrates a plant of 'ILVOHPPRM' with inflorescences in the middle stage of maturity, with pink coloration just beginning to show.
Figure 3:
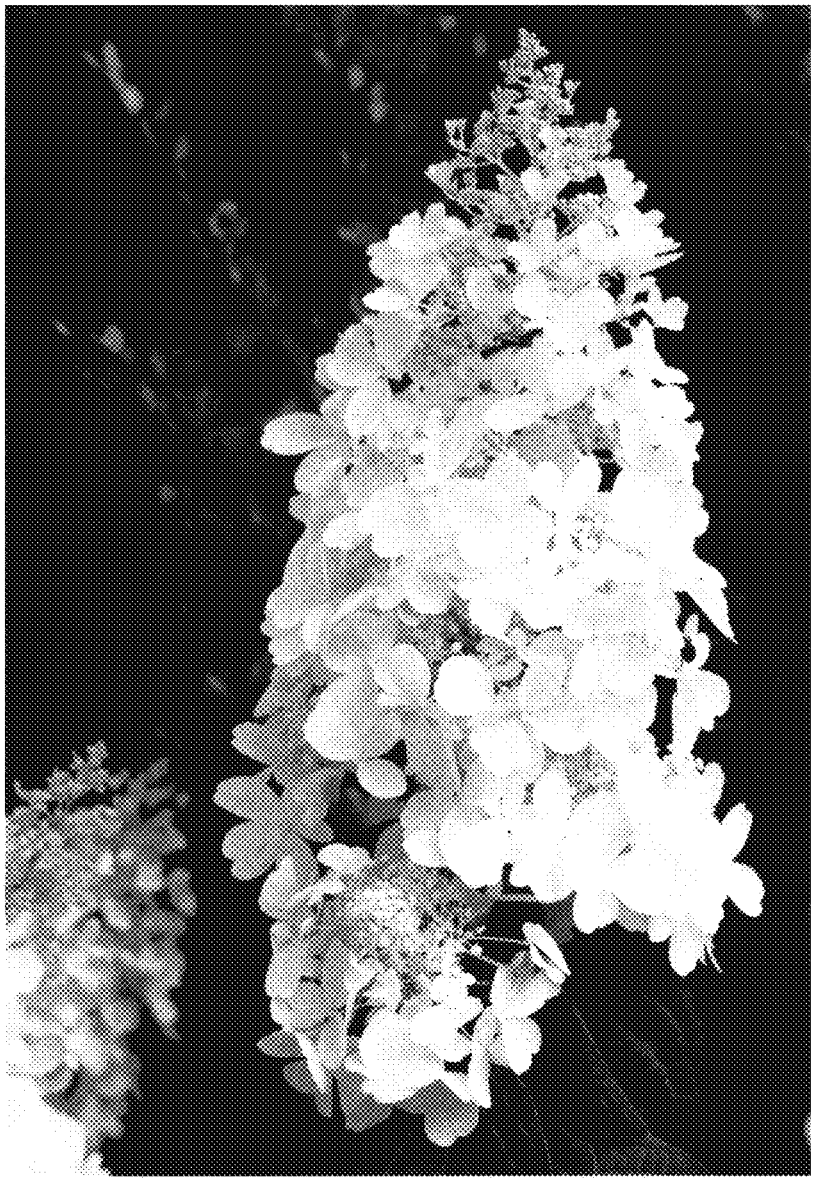
FIG. 3 illustrates in full color a close up of an inflorescence of 'ILVOHPPRM' in the earliest stage of maturity.
Figure 4:
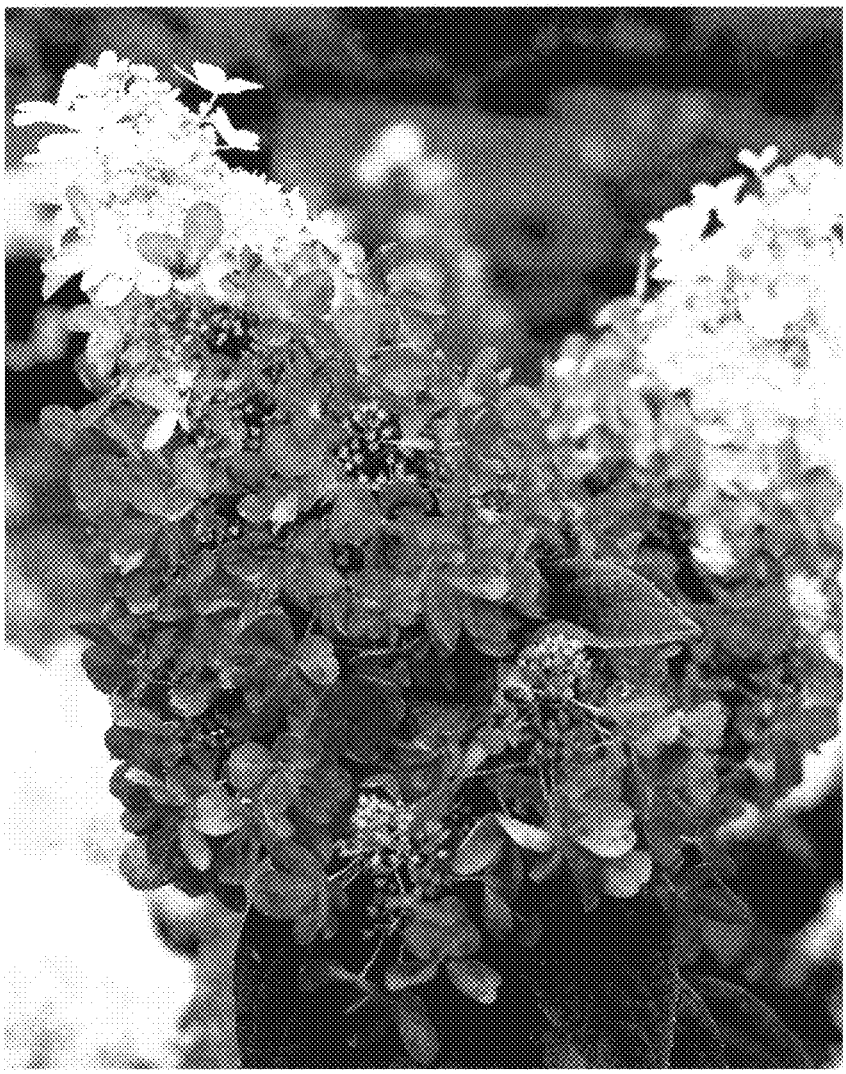
FIG. 4 illustrates in full color a close up of an inflorescence of 'ILVOHPPRM' in the middle stage of maturity, with both pink and white flowers.
Figure 5:
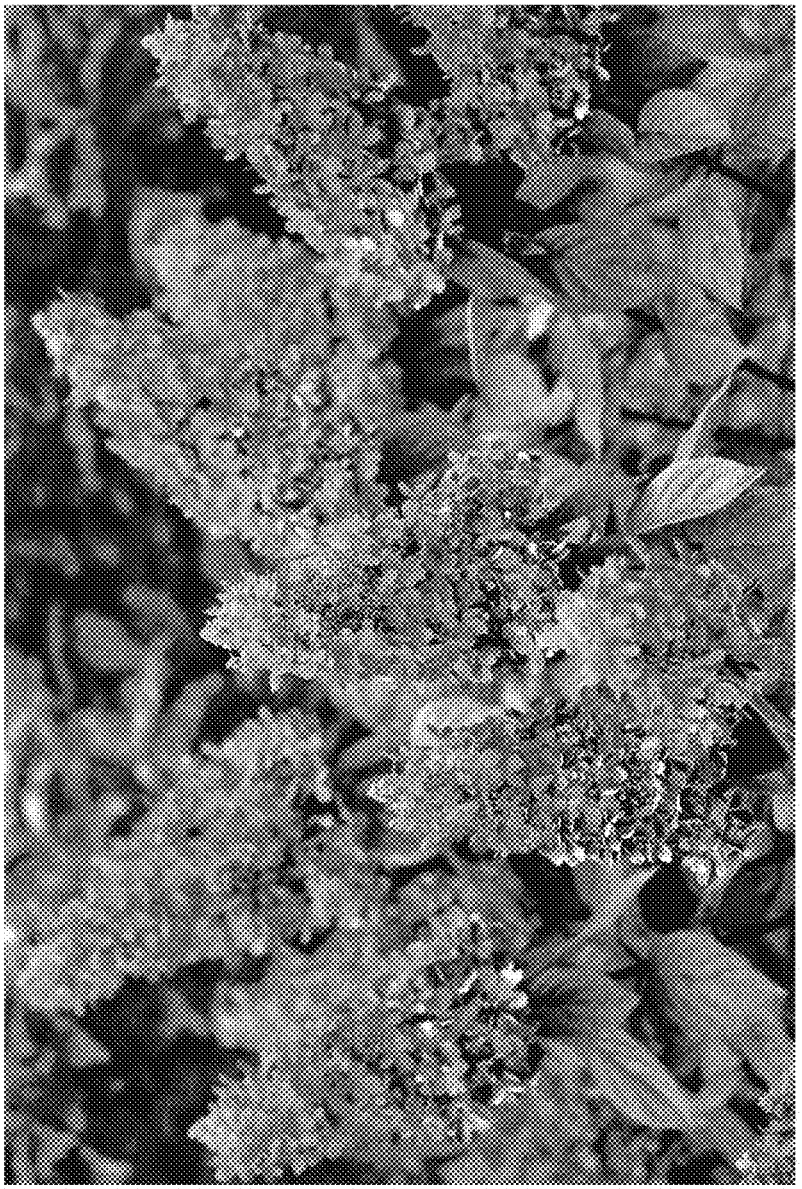
FIG. 5 illustrates in full color a close up view of an inflorescence at the full maturity, having turned dark pink.

In the following description, color references are made to The Royal Horticultural Society Colour Chart 2015, except where general terms of ordinary dictionary significance are used. The following observations and measurements describe 'ILVOHPPRM' plants grown in a poly-greenhouse in Grand Haven, Mich. The plants were about 2 to 3 years old. Temperatures ranged from 5° C. to 10° C. at night to 18° C. to 27° C. during the day. No artificial light, photoperiodic treatments were given to the plants. Measurements and numerical values represent averages of typical plant types.

Botanical classification: *Hydrangea* x *paniculata* 'ILVOHPPRM'.

PROPAGATION

Typical method: Softwood cuttings.
Root initiation: 20 days at 20° C. during summer.
Time to produce rooted cutting: About 2 months at 20° C. during summer.
Roots: Dense, freely branching, fibrous, thick to thin. Creamy white to brown in color, not accurately measured with RHS chart.

PLANT

Growth habit: Upright, upwards.
Height: 90 to 100 cm.
Plant spread: 70 cm.
Pot size of plant described: 3 gallon container.
Age of plant described: Approximately 2 to 3 years.
Growth rate: Good.
Plant vigor: Vigorous.
Stem:
- *Branching.*—Basal.
- *Number of lateral branches.*—10.
- *Shape.*—Rounded.
- *Color.*—Immature: RHS Greyed-Red 179A. Mature: RHS Brown 200B with Brown 200D lenticels.
- *Length.*—80 cm.
- *Width.*—7 mm.
- *Aspect.*—70 to 90°.
- *Strength.*—Quite strong.
- *Pubescence.*—None.
- *Internode length.*—7 to 10 cm.

FOLIAGE

Leaf:
- *Arrangement.*—Whorl (3 leaves equally spaced around each node).
- *Shape.*—Elliptic.
- *Length.*—12.5 cm.
- *Width.*—6 cm.
- *Apex.*—Acuminate.
- *Base.*—Obtuse.
- *Margin.*—Serrulate.
- *Texture of top surface.*—Roughly textured with coarse, bristly hairs.
- *Texture of bottom surface.*—Roughly textured with coarse, bristly hairs and pronounced venation.
- *Pubescence.*—Yes, both sides.
- *Color.*—Young foliage upper side: RHS Green NN137B. Young foliage under side: RHS Greyed-Green 194A. Mature foliage upper side: RHS Green NN137B. Mature foliage, under side: RHS Greyed-Green 194A.

Venation:
- *Type.*—Pinnate.
- *Color.*—Upper side: RHS Yellow-Green N144D. Under side: RHS Greyed-Green 194A with tinges of Greyed-Purple 183A closer to petiole.

Petiole:
- *Length.*—2 cm.
- *Width.*—3 mm.
- *Color.*—Upper side: RHS Greyed-Purple 183A. Under side: RHS Greyed-Purple 183A.
- *Texture.*—Upper side: Lightly pubescent. Under side: Lightly pubescent.

INFLORESCENCE

Natural flowering season: Summer.
Inflorescence type: Mophead.
Panicle:
- *Shape.*—Conical.
- *Height.*—25 to 30 cm.
- *Diameter.*—15 to 18 cm.

Fragrance: Sweet and floral, moderate intensity.
Sterile flowers:
- *Flowers per inflorescence.*—300 to 400.
- *Aspect.*—Outward to slightly upright.
- *Shape.*—Cruciform/stellate.
- *Length.*—4 to 5 cm.
- *Diameter.*—4 to 5 cm.
- *Depth.*—3 mm.
- *Persistent or self-cleaning.*—Persistent.

Bud:
- *Length.*—4 mm.
- *Diameter.*—3 mm.
- *Shape.*—Obovate.
- *Color.*—RHS White NN155A.

Petals:
- *Number per flower.*—3 to 4.
- *Shape.*—Narrowly elliptic.
- *Tip.*—Acute.
- *Base.*—Truncate.
- *Margin.*—Entire.
- *Length.*—4 mm.
- *Width.*—2 mm.
- *Texture.*—Upper side: Smooth. Under side: Smooth.
- *Color.*—When Opening, Upper side: RHS White NN155B. When Opening, Under side: RHS White NN155B. Fully Opened, Upper side: RHS White NN155B. Fully Opened, Under side: RHS White NN155B.

Sepal:
*Number.*—4 to 5.
*Arrangement.*—Cruciform/stellate.
*Shape.*—Elliptic.
*Tip.*—Emarginate.
*Base.*—Cuneate.
*Margin.*—Entire.
*Length.*—2 to 3 cm.
*Width.*—1.5 to 2.25 cm.
*Texture.*—Upper side: Soft and silky. Under side: Soft and silky.
*Color.*—When Opening, Upper side: RHS Green-Yellow 1D. When Opening, Under side: RHS Green-Yellow 1D. Fully Opened, Upper side: RHS White 155A. Fully Opened, Under side: RHS White 155A. Fading, Upper side: RHS Red-Purple 65D mixed with 63A. Fading, Under side: RHS Red-Purple 65D mixed with 63A.

Pedicel:
*Length.*—2 cm.
*Diameter.*—2 mm.
*Angle.*—45°.
*Strength.*—Good, flexible.
*Texture.*—Lightly pubescent.
*Color.*—RHS White 155A.

Fertile flowers:
*Flowers per inflorescence.*—Around 100.
*Aspect.*—Upright and outward.
*Shape.*—Stellate.
*Length.*—1 cm.
*Diameter.*—1 cm.
*Depth.*—4 mm.
*Persistent or self-cleaning.*—Self-cleaning.

Bud:
*Length.*—4 mm.
*Diameter.*—3 mm.
*Shape.*—Obovate.
*Color.*—RHS White NN155A.

Petals:
*Number per flower.*—5.
*Arrangement.*—Stellate.
*Shape.*—Narrowly elliptic.
*Tip.*—Acute.
*Base.*—Flat-bottomed.
*Margin.*—Entire.
*Length.*—4 mm.
*Width.*—2 mm.
*Texture.*—Upper side: Smooth. Under side: Smooth.
*Color.*—When Opening, Upper side: RHS White NN155B. When Opening, Under side: RHS White NN155B. Fully Opened, Upper side: RHS White NN155B. Fully Opened, Under side: RHS White NN155B.

Sepal: None.

Pedicel:
*Length.*—2 mm.
*Diameter.*—1 mm.
*Angle.*—45°.
*Strength.*—Good, flexible.
*Texture.*—Lightly pubescent.
*Color.*—RHS White 155A.

REPRODUCTIVE ORGANS

Sterile flower:
Stamens:
*Number.*—About 8.
*Filament color.*—RHS White NN155B.
*Filament length.*—3 mm.
Anthers:
*Length.*—1 mm.
*Shape.*—Rounded.
*Color.*—RHS Yellow-White 158B.
*Pollen.*—Moderate.
*Pollen color.*—RHS Yellow-White 158C.
Pistil:
*Number.*—1.
*Length.*—1 mm.
Stigma:
*Shape.*—Bi-lobed.
*Color.*—RHS Yellow-White 158C.
*Style length.*—0.5 mm.
*Style color.*—RHS Yellow-White 158C.

Fertile flower:
Stamen:
*Number.*—10.
*Filament length.*—5 mm.
*Filament color.*—RHS White NN155B.
Anther:
*Shape.*—Rounded.
*Length.*—1 mm.
*Color.*—RHS Yellow-White 158B.
*Pollen amount.*—Moderate.
*Pollen color.*—RHS Yellow-White 158C.
Pistil:
*Number.*—1.
*Length.*—2 mm.
Stigma:
*Shape.*—Tri-lobed.
*Color.*—RHS Yellow-White 158C.
*Style length.*—1 mm.
*Style color.*—RHS Yellow-White 158C.

OTHER CHARACTERISTICS

Disease resistance: Neither resistance nor susceptibility to the normal diseases and pests of *Hydrangea* has been observed.

Drought tolerance and cold tolerance: The new cultivar can tolerate cold temperatures to approximately −31° C. and tolerates an upper temperature range to at least 38° C.

Fruit/seed production: Not observed to date.

What is claimed is:

1. A new and distinct cultivar of *Hydrangea* plant named 'ILVOHPPRM' as herein illustrated and described.

* * * * *